(12) United States Patent
Huddleston et al.

(10) Patent No.: US 9,600,881 B2
(45) Date of Patent: Mar. 21, 2017

(54) METHODS, SYSTEMS AND COMPUTER READABLE STORAGE MEDIA STORING INSTRUCTIONS FOR IMAGING AND DETERMINING INFORMATION ASSOCIATED WITH REGIONS OF THE BRAIN

(71) Applicant: EMORY UNIVERSITY, Atlanta, GA (US)

(72) Inventors: Daniel E. Huddleston, Marietta, GA (US); Xiaoping P Hu, Tucker, GA (US); Sinyeob Ahn, Pacheco, CA (US); Xiangchuan Chen, Tucker, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/395,140

(22) PCT Filed: Mar. 13, 2013

(86) PCT No.: PCT/US2013/030894
§ 371 (c)(1),
(2) Date: Oct. 17, 2014

(87) PCT Pub. No.: WO2013/165573
PCT Pub. Date: Nov. 7, 2013

(65) Prior Publication Data
US 2015/0125057 A1     May 7, 2015

Related U.S. Application Data

(60) Provisional application No. 61/642,923, filed on May 4, 2012, provisional application No. 61/660,390, filed on Jun. 15, 2012.

(51) Int. Cl.
*G06K 9/00*     (2006.01)
*G06T 7/00*     (2006.01)
(Continued)

(52) U.S. Cl.
CPC ............ *G06T 7/0014* (2013.01); *A61B 5/055* (2013.01); *G01R 33/5605* (2013.01);
(Continued)

(58) Field of Classification Search
USPC ....... 382/100, 103, 107, 128–134, 162, 168, 382/172–173, 181, 184, 199, 232, 254,
(Continued)

(56) References Cited

U.S. PATENT DOCUMENTS

| | | | |
|---|---|---|---|
| 2010/0239142 A1* | 9/2010 | Dannels | G01R 33/246 382/131 |
| 2011/0018537 A1* | 1/2011 | Warntjes | G01R 33/5602 324/309 |

(Continued)

OTHER PUBLICATIONS

Kenichi Kashihara et al. Reduction of neuromelanin-positive nigral volume in patients with MSA, PSP and CBD, Internal Medicine 50: 1683-1687, 2011, [online]. Retrieved from the Internet: internalmedicine. 50.5101 >, abstract.*

(Continued)

*Primary Examiner* — Seyed Azarian
(74) *Attorney, Agent, or Firm* — Emory Patent Group

(57) ABSTRACT

Methods, systems and computer-readable storage mediums relate to imaging techniques of a region, for example, the brain, with magnetization transfer contrast (MTC°) effects with less specific absorption rate (SAR). The methods, systems and computer-readable storage mediums may include acquiring MR image data from at least one magnetic resonance (MR) scan that includes a pre-pulse signal and a pulse sequence. The pre-pulse signal may be less than 500°, e.g., from about 150° to 425°, and the pulse-sequence may be a gradient echo based sequence. The methods, systems and computer-readable storage mediums may include generating information associated with an image of at least one region of a subject. The information may include quantita-
(Continued)

tive or qualitative information of a region of a brain. The quantitative information may include volume information, contrast to noise ratio information, number of voxels, as well as other information.

15 Claims, 7 Drawing Sheets

(51) Int. Cl.
    *A61B 5/055*     (2006.01)
    *G01R 33/56*     (2006.01)
    *G01R 33/565*     (2006.01)
    *A61B 5/05*     (2006.01)
    *A61B 5/00*     (2006.01)

(52) U.S. Cl.
    CPC ...... *G01R 33/56509* (2013.01); *G06T 7/0012* (2013.01); *A61B 5/4064* (2013.01); *A61B 5/4082* (2013.01); *A61B 5/4088* (2013.01); *G01R 33/5608* (2013.01); *G06T 2207/10088* (2013.01); *G06T 2207/30016* (2013.01)

(58) Field of Classification Search
    USPC ............... 382/274, 276, 291, 305, 312, 287; 324/309; 600/410, 420; 378/4, 21
    See application file for complete search history.

(56) References Cited

U.S. PATENT DOCUMENTS

| | | | | |
|---|---|---|---|---|
| 2011/0213237 | A1* | 9/2011 | Park ........................ | A61B 5/055 600/410 |
| 2012/0062227 | A1* | 3/2012 | Stuber ................ | G01R 33/4828 324/309 |
| 2012/0271159 | A1* | 10/2012 | Song ................... | G01R 33/5601 600/420 |

OTHER PUBLICATIONS

Ahlskog, J. "Beating a dead horse: Dopamine and Parkinson disease." Neurology, 2007; 69(17): 1701-1711.
Ahn et al. "Neuromelanin MR Imaging: Detection of Locus Coeruleus Using T1 Weighted Gradient Echo Imaging." Proceedings of the International Society for Magnetic Resonance in Medicine, ISMRM, 20th Annual Meeting and Exhibition, Melbourne, Australia, 2012: 2326.
Ashton-Jones et al. "Adaptive Gain and the Role of the Locus Coeruleus-Norepinephrine System in Optimal Performance." The Journal of Comparative Neurology, 2005; (493) 99-110.
Benarroch, E. "The locus ceruleus norepinephrine system: Functional organization and potential clinical significance." Neurology, 2009; 73(20): 1699-1704.
Bouret et al. "Network reset: a simplified overarching theory of locus coeruleus noradrenaline function." Trends in Neurosciences, 2005; 28(11): 574-582.
Braak et al. "Staging of brain pathology related to sporadic Parkinson's disease." Neurobiology of Aging, 2003; 24 (2): 197-211.
Chan-Palay et al. "Alterations in Catecholamine Neurons of the Locus Coeruleus in Senile Dementia of the Alzheimer Type and in Parkinson's Disease With and Without Dementia and Depression." The Journal of Comparative Neurology, 1989; 287(3): 373-392.
Chaudhuri et al. "Non-motor symptoms of Parkinson's disease: dopaminergic pathophysiology and treatment." Lancet Neurology, 2009; 8(5): 464-474.
Chen et al. "Simultaneous imaging of locus coeruleus and substantia nigra with a quantitative neuromelanin MRI approach." Magnetic Resonance Imaging, 2014; 32(10): 1301-1306.
Deoni, S. "High-Resolution T1 Mapping of the Brain at 3T with Driven Equilibrium Single Pulse Observation of T1 with High-Speed Incorporation of RF Field Inhomogeneities (DESPOT1-HIFI)." Journal of Magnetic Resonance Imaging, 2007; 26(4): 1106-1111.
Dubowitz et al. "Direct comparison of visual cortex activation in human and non-human primates using functional magnetic resonance imaging." Journal of Neuroscience Methods, 2001; 107(1-2): 71-80.
Eidelberg, D. "Metabolic brain networks in neurodegenerative disorders: a functional imaging approach." Trends in Neuroscience, 2009; 32(10): 548-557.
German et al. "The Human Locus Coeruleus: Computer Reconstruction of Cellular Distribution." The Journal of Neuroscience, 1988; 8(5): 1776-1778.
German et al. "Disease-specific Patterns of Locus Coeruleus Cell Loss." Annals of Neurology, 1992; 32(5): 667-676.
Hawkes et al. "A timeline for Parkinson's Disease." Parkinsonism and Related Disorders, 2010; 16(2): 79-84.
Huddleston et al. "729: Quantitative in vivo MRI measurement of locus coeruleus degeneration in patients with Parkinson's disease." Movement Disorders, 2012; 27, Suppl. 1: S239.
Huddleston et al. "Quantitative in vivo MRI measurement of locus coeruleus degeneration in patients with Parkinson's disease." Poster, Session 3, Jun. 19, 2012, Sixteenth International Congress of Parkinson's Disease and Movement Disorders, Dublin, Ireland, Jun. 17-21, 2012.
Inglese et al. "Global average gray and white matter N-acetylaspartate concentration in the human brain." NeuroImage, 2008; 41(2): 270-276.
Karahan et al. "Studying Familiarity of Different Stimulus Types." Proceedings of the International Society For Magnetic Resonance in Medicine, ISMRM, 17th Annual Meeting and Exhibition, Honolulu, Hawaii, 2009: 1701.
Kashihara et al. "Reduction of Neuromelanin-Positive Nigral Volume In Patients with MSA, PSP and CBD." Internal Medicine, 2011; 50: 1683-1687.
Keren et al. "In vivo mapping of the human locus coeruleus." NeuroImage, 2009: 47(4): 1261-1267.
Leentjens et al. "Higher Incidence of Depression Preceding the Onset of Parkinson's Disease: A Register Study." Movement Disorders, 2003; 18(4): 414-418.
Marek et al. "Can we image premotor Parkinson disease?" Neurology, 2009; 72 (Suppl. 2): S21-S26.
Menke et al. "MRI characteristics of the substantia nigra in Parkinson's disease: A combined quantitative T1 and DT1 study." NeuroImage, 2009; 47(2): 435-441.
Minzenberg et al. "Modafinil Shifts Human Locus Coeruleus to Low-Tonic, High-Phasic Activity During Functional MRI." Science, 2008; 322(5908): 1700-1702.
Minzenberg et al. "Response to Comment on 'Modafinil Shifts Human Locus Coeruleus to Low-Tonic, High-Phasic Activity During Functional MRI.'" Science, 2010; 328(5976): 309-b.
Nakane et al. "Visualization of Neuromelanin in the Substantia Nigra and Locus Ceruleus at 1.5T Using a 3D-gradient Echo Sequence with Magnetization Transfer Contrast." Magnetic Resonance in Medical Sciences, 2008; 7(4): 205-210.
Papaptropoulos et al. "The effect of depression on motor function and disease severity of Parkinson's disease." Cinical Neurology and Neurosurgery, 2006; 108(5): 465-469.
Pintor et al. "Response to 4-month treatment with reboxetine in Parkinson's disease patients with a major depressive episode." General Hospital Psychiatry, 2006; 28(1): 59-64.
Rommelfanger et al. "Reduced MPTP toxicity in noradrenaline transporter knockout mice." Journal of Neurochemistry, 2004; 91(5): 1116-1124.
Rommelfanger et al. "Norepinephrine: The readheaded stepchild of Parkinson's disease." Biochemical Pharmacology, 2007; 74(2): 177-190.
Sasaki et al. "Neuromelanin magnetic resonance imaging of locus ceruleus and substantia nigra in Parkinson's disease." Neuroreport, 2006; 17(11): 1215-1218.
Sasaki et al. "Monoamine neurons in the human brain stem: anatomy, magnetic resonance imaging findings, and clinical implications." Neuroreport, 2008; 19(17): 1649-1654.

(56) References Cited

OTHER PUBLICATIONS

Savica et al. "When Does Parkinson Disease Start?" Archives of Neurology, 2010; 67(7): 798-801.
Schwarz et al. "T1-Weighted MRI Shows Stage-Dependent Substantia Nigra Signal Loss in Parkinson's Disease." Movement Disorders, 2011; 26(9): 1633-1638.
Shibata et al. "Reduced signal of locus ceruleus in depression in quantitative neuromelanin magnetic resonance imaging." Neuroreport, 2007; 18(5): 415-418.
Stern et al. "Reaction Time and Vigilance in Parkinson's Disease: Possible Role of Altered Norepinephrine Metabolism." Archives of Neurology, 1984; 41(10): 1086-1089.
Sulzer et al. "Neuromelanin biosynthesis is driven by excess cytosolic catecholamines not accumulated by synaptic vesicles." Proceedings of the National Academy of Sciences of the United States of America, 2000; 97(22): 11869-11874.
Taylor et al. "Nonmotor Symptoms of Parkinson's Disease Revealed in an Animal Model with Reduced Monoamine Storage Capacity." The Journal of Neuroscience, 2008; 29(25): 8103-8113.
Vaillancourt et al. "High-resolution diffusion tensor imaging in the substantia nigra of de novo Parkinson disease." Neurology, 2009; 72(16): 1378-1384.
Valentino et al. "Convergent regulation of locus coeruleus activity as an adaptive response to stress." European Journal of Pharmacology, 2008; 583(2-3): 194-203.
Wichmann et al. "Uptake, Release and Modulation of Release Of Noradrenaline in Rabbit Superior Colliculus." Neuroscience, 1988; 26(2): 621-634.
Zarow et al. "Neuronal Loss is Greater in the Locus Coeruleus Than Nucleus Basalis and Substantia Nigra in Alzheimer and Parkinson Diseases." Archives of Neurology, 2003; 60(3): 337-341.
Zecca et al. "The role of iron and copper molecules in the neuronal vulnerability of locus coeruleus and substantia nigra during aging." Proceedings of the National Academy of Sciences of the United States of America, 2004; 101(26): 9843-9848.
EPC Search Report for European Application No. 13784304.1 issued on Apr. 22, 2016.

* cited by examiner

900

METHODS, SYSTEMS AND COMPUTER READABLE STORAGE MEDIA STORING INSTRUCTIONS FOR IMAGING AND DETERMINING INFORMATION ASSOCIATED WITH REGIONS OF THE BRAIN

CROSS REFERENCE TO RELATED APPLICATION

This application is a 371 U.S.C filing of PCT/US2013/030894 filed on Mar. 13, 2013, and claims the benefit of priority to U.S. Provisional Application Ser. No. 61/642,923 filed on May 4, 2012, and U.S. Provisional Application Ser. No. 61/660,390 filed on Jun. 15, 2012 which are hereby incorporated by this reference in their entireties.

BACKGROUND

Monoamine neurons, such as dopaminergic, noradrenergic, and serotoninergic neurons, play important roles in the regulation of the motor, cognitive, affective, and arousal functions. These neurons are located in the brain stem, for example, in the substantia nigra pars compacta (SN), locus ceruleus (LC), ventral tegmental area (VTA), and raphe nuclei (RN).

There are many disorders associated with abnormalities and dysfunction for monoamine neurons. Many forms of neurodegenerative diseases, for example, Parkinson's disease, progressive supranuclear palsy, Pick's disease, Alzheimer's disease, and Down's syndrome, are characterized by pathological changes in the brain stem. For example, neuronal loss of the SN and LC has been associated with Parkinson's disease and neuronal loss in the LC has been associated with Alzheimer's disease. Additionally, dysregulation of monoamine neurons, for example, in the noradrenergic, serotoninergic, and/or dopaminergic systems have been associated with psychiatric disorders, for example, depression and schizophrenia. See, e.g., M. Sasaki et al., Neuroreport, 2008 Nov. 19; 19(17):1649-54.

Magnetic Resonance (MR) images have been identified as one way to detect pathological changes in the brain stem. However, imaging the brain stem has been difficult due to its size and location and/or contrast resolution.

Thus, there is a need for imaging methods, computer-readable storage mediums, and systems that can accurately image the brain stem of a subject.

SUMMARY

The disclosure relates to systems, methods, and computer-readable mediums storing instructions for generating MR images, for example, of a brain stem based on magnetization transfer contrast (MTC) effects. In some embodiments, the disclosure relates to systems, methods, and computer-readable mediums storing instructions for processing MR image data to determine and/or classify qualitative and/or quantitative information of a region of interest (also referred to as "region").

In some embodiments, the disclosure may relate to a method for generating MR images. The method may include acquiring image(s) of a region of interest of a subject. The images may include acquiring MR images using a 3T system. The acquiring may include applying or causing an application of a pre-pulse signal to a region of interest of the subject. In some embodiments, the region of interest may include region(s) of a brain of a subject, for example, a brain stem of a subject. In some embodiments, the pre-pulse signal may be specific to the MTC effects of the neuromelanin pigment and/or region(s) of interest of the treatment site, for example, the brain stem of a brain of the subject. In some embodiments, the pre-pulse may include parameters sufficient to saturate the region to be imaged.

In some embodiments, the pre-pulse signal may have a flip angle of less than about 500°. In some embodiments, the flip angle may be less than about 350°. In some embodiments, the flip angle may be between about 150° and 425°. In some embodiments, the flip angle may be less than about 325°. In some embodiments, the flip angle may between 250° and 325°. In some embodiments, the flip angle may between 275° and 325°. In some embodiments, the flip angle may be about 300°. In some embodiments, the flip angle may be less than 300°.

In some embodiments, the pre-pulse signal may be applied for a duration of about 10 ms. In some embodiments, the duration may be more or less than 10 ms.

In some embodiments, the method may further include applying a pulse sequence to the region after the pre-pulse. The pulse sequence may be based on a gradient echo sequence protocol. In some embodiments, the sequence may be 2D. In some embodiments, the parameters of the pulse sequence may be based on any known gradient echo sequence protocol. In some embodiments, the parameters of the pulse sequence may be based on a known turbo spin echo protocol specific to the region of interest, for example, the brain stem and/or neuromelanin pigment.

In some embodiments, the steps of applying the pre-pulse and pulse sequence may be repeated for each slice. In some embodiments, the steps of applying the pre-pulse and pulse sequence may be repeated until all the data and/or measurements necessary to generate the image is acquired. In some embodiments, the steps may be repeated until a predetermined number of slices and/or MR data is obtained.

In some embodiments, the method may include acquiring MR data. In some embodiments, the method may further include generating image data. In some embodiments, the generating may include processing the image data. In some embodiments, the processing the image data may include segmenting the image data.

In some embodiments, the method may include determining quantitative information of the region or a portion of the region. The determining may include determining quantitative information associated with the segmented image data. In some embodiments, the method may optionally include classifying the quantitative information according to a disease state. The disease state may include but is not limited to Parkinson's disease, progressive supranuclear palsy, Pick's disease, Alzheimer's disease, and Down's syndrome, as well as psychiatric disorders. The disease state may be based on a stored scale of disease states. In some embodiments, the stored scale may correspond to the progression of the disease (e.g., Parkinson's disease, progressive supranuclear palsy, Pick's disease, Alzheimer's disease, and Down's syndrome, as well as psychiatric disorders).

In some embodiments, the method may include outputting the image data and/or information. In some embodiments, the information may include any one, some or all, but is not limited to the quantitative information of the region, the classification of the quantitative information, a comparison with previous quantitative information, and the like. In some embodiments, the outputting may include but is not limited to displaying the image data and/or quantitative information, printing the image data and/or quantitative information, and storing the image data and/or volume information remotely or locally. In other embodiments, the image data and/or quantitative information may be forwarded for further processing.

In some embodiments, the quantitative information may include at least one of volume information, number of voxels, or contrast-to-noise ratio (CNR) information. In some embodiments, the CNR (or MEAN CNR) and number of voxel may substantially correspond to amount of neuromelanin in the region and a number of neurons that contain neuromelanin, respectively.

In some embodiments, the method may include segmenting the image data; and determining the contrast-to-noise ratio.

In some embodiments, the disclosure may relate to a method for generating information associated with an image of at least one region of a subject. The method may include determining at least quantitative information of the region from image data, the quantitative information include contrast-to-noise ratio information; and outputting the information. In some embodiments, the method may include processing the image data; wherein the processing includes generating a binary map, wherein voxels of the binary map with $B_{voxel}=1$ substantially corresponds to neuronal tissue containing neuromelanin.

In some embodiments, the disclosure may relate to processing MR data to determine and/or classify quantitative and/or qualitative information of the region. The region may include the brain stem of the subject. In some embodiments, the region may include but is not limited to the substantia nigra pars compacta (SN), locus ceruleus (LC), ventral tegmental area (VTA), and raphe nuclei (RN).

In some embodiments, the method may include receiving image data. The image data may be acquired by a 3T MRI system from a MR scan that includes a prepulse signal and a pulse sequence according to a gradient echo imaging protocol, according to embodiments. In some embodiments, the image data may include a plurality of signal measurements acquired by a MR scan. In some embodiments, the image data may include a plurality of scans of a brain of a subject.

In some embodiments, the method may include processing the image data. The processing may include processing the image data to register the data to remove head motion artifact. In some embodiments, the processing may include selecting one signal measurement without head motion artifact from the received image data. The method may include aligning all of the other measurements to the selected measurement. In some embodiments, the aligning step may be based on a linear registration technique. In some embodiments, the method may include discarding any of the aligned measurements that are above a certain threshold, the certain threshold corresponding to severe head motion. In some embodiments, the method may include averaging the remaining aligned measurements.

In some embodiments, the processing may additionally or alternatively include processing the image data to aligning the image data in a common space. In some embodiments, the aligning step may include a step of aligning each image of the subject to acquired T1 images. The processing may include converting the image data into the common space. The converting may include converting the T1 images into the common space. The converting may also include converting the images of the subject into the same common space based on the aligning and converting steps. The processing may further include generating a mask of the at least one region of the brain, for example, the SN and/or LC regions. In some embodiments, the generating may include binarizing the region(s) as a mask on the neuromelanin images in the common space.

In some embodiments, the method may further include analyzing the received image data. The analyzing may include determining information from the image data. The information may be quantitative and/or qualitative information or measurements of at least one region (e.g., the LC and/or SN regions of the brain). The information may include but is not limited to disease state, quantitative information, metabolic information or measurements, physiologic information or measurements, as well as multimodal information or measurements.

In some embodiments, the analyzing may include additional processing. The analyzing may include segmenting the image data. In some embodiments, the image data may be aligned image data. In some embodiments, the segmenting may include defining a number (e.g., two) regions of interest (ROI)s. The segmenting may be global region-based segmenting.

In some embodiments, the analyzing may include determining quantitative information of at least one region. In some embodiments, the quantitative information may include any one, some or all, but is not limited to the quantitative of the region, the classification of the quantitative, a comparison with previous quantitative information, and the like. In some embodiments, the quantitative information may include at least one of volume information, number of voxels, or contrast-to-noise ratio (CNR) information. In some embodiments, the CNR (or MEAN CNR) and number of voxel may substantially correspond to amount of neuromelanin in the region and a number of neurons that contain neuromelanin, respectively. In some embodiments, the volume information may be the product of the number of segmented voxels and the volume of a single voxel.

In some embodiments, the method may include a step of classifying the information. In some embodiments, the information may be compared to previous information of the subject, for example, to provide information regarding the progression of the disease. In some embodiments, the information may be compared to information associated with many subjects, e.g., an atlas. The comparing may include comparing the information to at least one predetermined range, each range being associated with a different disease state and/or progression of the disease state. The disease state may include but is not limited to Parkinson's disease, progressive supranuclear palsy, Pick's disease, Alzheimer's disease, and Down's syndrome, as well as psychiatric disorders.

In some embodiments, the method may include outputting the results. In some embodiments, the results may include the information, the image data, and at least one generated image. The information may include any one, some or all, but is not limited to the quantitative and/or qualitative information associated with the LC and/or SN of the subject, the classification of the information with respect to previous information of the subject and/or prestored information associated with different disease states and/or progression of the disease state, and the like. In some embodiments, the outputting may include but is not limited to displaying the results, printing the results, and storing the results remotely or locally. In other embodiments, the results may be transmitted for further processing.

In some embodiments, the disclosure may relate to a method of generating an atlas. The atlas may be specific to regions of the brain, for example, the LC and/or the SC regions.

In some embodiments, the processed image data may be used to generate an atlas for the SN and/or LC. In some embodiments, the method may include a step of receiving image data for a plurality of subjects. In some embodiments, the image data may have been already processed to generate masks for the SN and/or LC. The method may include combining the image data for a plurality of subjects in the common space. In some embodiments, the method may include generating an atlas. The generating may include overlaying the combined masks onto T1 images in the common space.

The method may include outputting the atlas. In some embodiments, the outputting may include but is not limited to displaying the atlas (e.g., combined masks onto 2D T1 images), printing the atlas, and storing the atlas remotely or locally. In other embodiments, the atlas may be transmitted for further processing.

In some embodiments, the method(s) may be an automatic method. In some embodiments, the method(s) may be performed by a computer having a memory and a processor. In some embodiments, the method(s) may be performed by an image acquisition system, for example, an MR system capable of using a gradient echo imaging protocol. In some embodiments, the MR system may be a 3T system.

In some embodiments, a method may generate an image of a brain stem of a subject. The method may include: acquiring image data of the brain stem using a 3T MRI system, the acquiring including applying a pre-pulse signal that has a flip angle between about 150° and 425° and pulse sequence according to a gradient echo imaging protocol; processing the image data; and generating the image.

In some embodiments, a computer-readable storage medium may store instructions for generating MR images, determining quantitative information and/or classifying quantitative information. The instructions may include: applying a pre-pulse signal to a region; applying a pulse sequence according to a gradient echo imaging protocol to the region; and acquiring MR image data. In some embodiments, the pre-pulse signal may have a flip angle of less than about 500°. In some embodiments, the flip angle may be between 150° and 425°. In some embodiments, the flip angle may be between about 250° and 350°. In some embodiments, the flip angle may be less than about 325°. In some embodiments, the flip angle may between 250° and 325°. In some embodiments, the flip angle may be between 275° and 325°. In some embodiments, the flip angle may be about 300°. In some embodiments, the flip angle may be less than 300°.

In some embodiments, the instructions optionally and/or alternatively may include any one, some or all of the following: processing the data; segmenting the processed data; determining information; and classifying the information.

In some embodiments, the processing may include instructions for outputting the information and/or image data.

In some embodiments, the disclosure may relate to a system may be configured to generate MR images, determine quantitative information and/or classifying quantitative information.

In some embodiments, the system may optionally include an MR system. The MR system may be capable of applying a prepulse signal and a pulse sequence according to a gradient echo imaging protocol to a region, according to embodiments. The MR system may be a 3T MR system.

In some embodiments, the system may include a processor. The processor may be configured to control an MR system. The system may be configured to apply a pre-pulse signal to a region; apply a pulse sequence to a gradient echo imaging protocol to the region after the pre-pulse signal; and acquire image data.

In some embodiments, the processor may be configured to process the image to determine the information associated with the region. In some embodiments, the processor may be configured to classify the information.

In some embodiments, the disclosure may relate to a method of diagnosing for a disease state including Parkinson's disease, progressive supranuclear palsy, Pick's disease, Alzheimer's disease, and Down's syndrome. The method including determining at least quantitative information of the region from image data, the quantitative information including contrast-to-noise ratio information; classifying the quantitative information.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
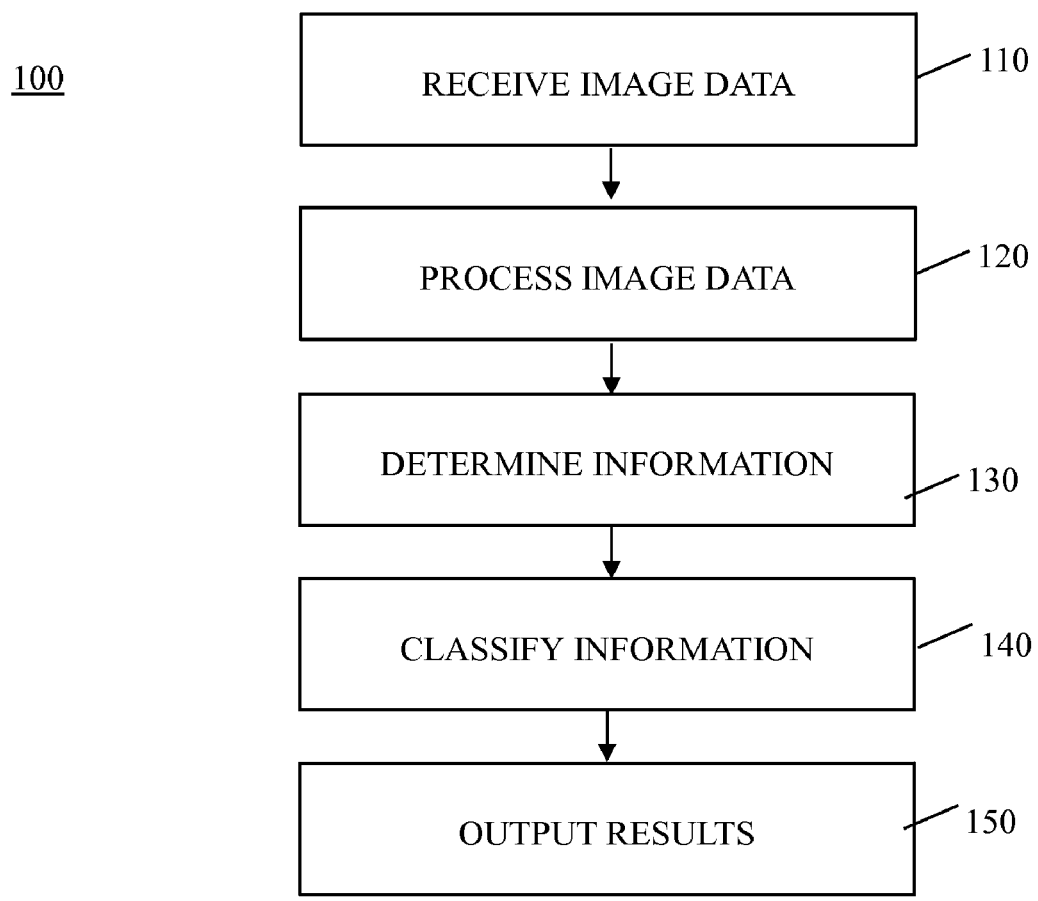
FIG. 1 shows a method to generate an image information of a brain according to embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The embodiments of the disclosure are described with respect to an image of the brain, and more specifically, imaging and analyzing the brain stem of a subject. The methods, systems, and the computer-readable storage mediums of the disclosure may analyze specific regions of interest, for example, regions of the brain stem including but not limited the substantia nigra pars compacta (SN), locus ceruleus (LC), ventral tegmental area (VTA), and raphe nuclei (RN). However, it should be understood that the disclosure is not limited to the brain, and these regions of the brain, and may be applied to other regions of the brain, as well as other regions of interest (e.g., anatomical landmarks).

The methods, systems, and the computer-readable storage mediums according to embodiments address the deficiencies of conventional MRI imaging and systems. The methods, systems, and the computer-readable storage mediums according to embodiments are directed to imaging techniques with magnetization transfer contrast (MTC) effects with less specific absorption rate (SAR).

The methods, systems, and the computer-readable storage mediums according to embodiments address the limitations of other methods that reach the specific absorption rate (SAR) safety limit. Previous reports of neuromelanin MRI contrast either with or without off-resonant RF prepulses reached the SAR safety limit. See, e.g., Michael J Minzenberg et al., "Response to Comment on 'Modafinil Shifts Human Locus Coeruleus to Low-Tonic, High-Phasic Activity During Functional Mri,'" Science, 328 (2010), 309b; Sasaki M, Shibata et al., "Neuromelanin Magnetic Resonance Imaging of Locus Ceruleus and Substantia Nigra in Parkinson's Disease," Neuroreport, 17 (2006), 1215-18; and T. Schwarz et al., "T1-Weighted Mri Shows Stage-Dependent Substantia Nigra Signal Loss in Parkinson's Disease," Mov Disord, 26 (2011), 1633-8. Because these sequences deliver high amounts of electromagnetic energy to subjects, and subjects with different body types reach the SAR limit at different points, a study group of subjects with differing body types will likely require differing numbers of slices and/or scan times (or other parameter changes) to comply with the SAR safety limit. This heterogeneity can introduce variability in noise characteristics that can degrade the quality of the dataset, and some subjects (those reaching the SAR limit more easily) will likely require significantly longer scans to cover both LC and SN. Thus, the methods and systems according to embodiments, which use a GRE sequence (lower SAR than TSE) and a moderate powered MTC pulse approach, remain well under the SAR safety limit, and thereby allow the same protocol to be applied to all subjects regardless of body type while acquiring the same number of slices and covering LC and SN in all subjects.

Additionally, the methods, systems, and the computer-readable storage mediums according to embodiments address the adverse effects of motion on image quality when imaging small neuromelanin containing structures. The methods and systems acquire separate measurements during scanning, with subsequent coregistration in post-processing. Intra-subject coregistration of NM-MRI signal measurement images based on anatomic landmarks reduces image blurring in LC and SN due to small amounts of motion. If a single measurement is significantly degraded by motion, it can be discarded. This approach differs from online averaging of multiple measurements, which does not afford the opportunity to coregister signal measurements to correct for motion, or to discard motion degraded measurements.

It will also be understood that the method steps may cause or control the operation of an image acquisition device, for example, an MRI imaging system. It will be further understood that although the methods of the embodiments are discussed with respect to the actions of an imaging system and/or computer, the methods may be implemented using computer software to cause or control an MRI imaging system and/or computer system to perform these actions. It will also be understood that the methods according to the disclosure may be used with other types of image acquisition devices.

Imaging Methods

The methods of the disclosure are not limited to the steps described herein. The steps may be individually modified or omitted, as well as additional steps may be added.

Unless stated otherwise as apparent from the following discussion, it will be appreciated that terms such as "averaging," "binarizing," "filtering," "combining," "reconstructing," "segmenting," "generating," "registering," "determining," "obtaining," "processing," "computing," "selecting," "estimating," "detecting," "tracking," "outputting," "applying," "classifying," "calculating" "receiving," or "acquiring," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

FIG. 1 illustrates a method 100 according to embodiments to analyze image data. In some embodiments, the method 100 may include a step 110 of receiving image data. In some embodiments, the image data may be MR image data of a brain of a subject. In some embodiments, the MR data may include a plurality of signal measurements acquired by a MR scan. In some embodiments, the image data may include a plurality of scans of a brain of a subject.

Figure 2:
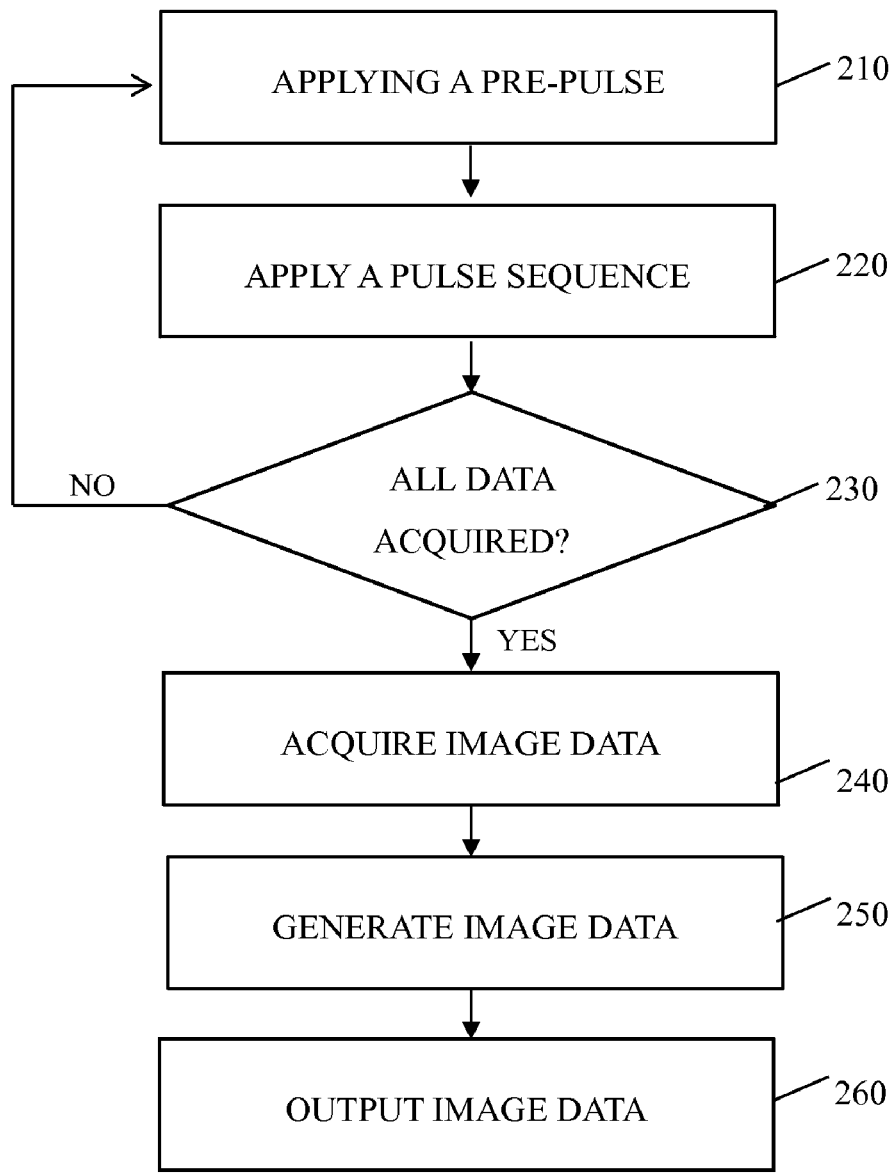
FIG. 2 shows a method to acquire image data of a region of a brain.

The MR data may be based on MTC effects. In some embodiments, the MR data may include a plurality of signal measurements acquired by a MR scan that includes a prepulse signal and a pulse sequence according to a gradient echo imaging protocol according to embodiments. FIG. 2 shows an example of a method 200 of acquiring MR image data according to embodiments. In other embodiments, the image data may be acquired by other methods.

Acquiring Method

FIG. 2 illustrates a method 200 according to embodiments to acquire image data of a region of interest (also referred to as "region"). In some embodiments, the method 200 may be for an execution on a magnetic resonance imaging (MRI) system comprising a magnet system and a controller for controlling the magnet system. In some embodiments, the MRI system may be a 3T MRI imaging system, for example, Siemens Tim Trio 3T MRI system. It will be understood that some steps of the method, for example, steps 210 and 220, may be based on a stored imaging protocol.

In some embodiments, the method 200 may include a step 210 of applying a pre-pulse signal. In some embodiments, the pre-pulse signal may be applied to a treatment site, for example, a brain of a subject. In some embodiments, the pre-pulse signal may be specific to the MTC effects of the neuromelanin pigment and/or region(s) of interest of the treatment site, for example, the brain stem of a brain of the subject. In some embodiments, the pre-pulse may include parameters sufficient to saturate the region to be imaged.

In some embodiments, the pre-pulse signal may have a flip angle of less than about 500°. In some embodiments, the flip angle may be less than about 425°. In some embodiments, the flip angle may be between about 150° and 425°. In some embodiments, the flip angle may be less than about 350°. In some embodiments, the flip angle may between about 250° and 350°. In some embodiments, the flip angle may between about 275° and 350°. In some embodiments, the flip angle may be about 300°. In some embodiments, the flip angle may be less than about 300°.

In some embodiments, the pre-pulse signal may be applied for a duration of about 10 ms. In some embodiments, the duration may be less than 10 ms. In some embodiments, the duration may be about 2-6 ms. In other embodiments, the duration may be more than 10 ms.

In some embodiments, the method 200 may further include a step 220 of applying a pulse sequence. The pulse sequence may be based on a gradient echo sequence protocol. In some embodiments, the echo may be 2D. In some embodiments, the parameters of the pulse sequence may be based on any known gradient echo sequence protocol. In some embodiments, the parameters of the pulse sequence may be based on a known turbo spin echo protocol specific to the region of interest, for example, the brain stem and/or neuromelanin pigment. In other embodiments, some or all of the parameters of the pulse sequence may be modified.

In some embodiments, the protocol may include the following parameters. In some embodiments, the minimum echo time (TE) may be less than about 10 ms. In some embodiments, the TE may be from about 2-6 ms. In other embodiments, the TE may be more than 10 ms.

In some embodiments, the minimum repetition per slice (TR/slice) may be within about 15-30 ms per slice. In some embodiments, the TR may be about 20-25 ms per slice.

In some embodiments, the image acquisition protocol flip angle may approximate the Ernst Angle. In some embodiments, the flip angle may be from about 40-45 degrees.

In some embodiments, there may be more than one signal measurement acquired. In some embodiments, at least three measurements may be acquired. In some embodiments, at least seven or more measurements may be acquired. By acquiring multiple measurements, small amounts of bulk motion may be addressed during post-processing (e.g., step 120). This allows signal measurements that contain significant motion artifact to be discarded.

In some embodiments, the effective slice orientation may be axially along the long axis of the brainstem, aligned perpendicular to the dorsal edge of the pons at midline (along the fourth ventricle). In other embodiments, the slice orientation may be different.

In some embodiments, the resolution may be within the range of about 0.2 mm×0.2 mm in plane to about 0.7 mm×0.7 mm in plane and the slice thickness may be within the range of about 1.5 mm to about 4.5 mm. In some embodiments, the resolution may be about 0.4 mm×0.4 MM in plane with a slice thickness of about 3 mm. In some embodiments, a high spatial resolution of about 0.4 mm may be desired.

In order to achieve a resolution of about 0.4 mm, a 512 matrix side may be administered along the readout direction and smaller sizes may be used along the phase-encoding direction when a small field-of-view (FOV) along the phase-encoding (PE) direction is used. This has a particular advantage for LC imaging. At a given total scan time, minimizing scan time per each measurement and accordingly having more number of measurements may decrease the possibility of contaminating each measurement by motion artifacts. Matrix size along both directions may be adjusted for different resolution ranges accordingly.

The number of slices and slice thickness may vary between subjects. The slices may be positioned to allow the most superior and inferior slices along the axis of the brainstem to be discarded as both edge slices show different image contrasts relative to other inner slices. In some embodiments, the number may be about 8-15 slices depending on the regions of interest. The slice thickness may be about 3 mm. For example, if imaging both LC and SN, about 15 slices may be acquired. If imaging the SN or LC only, about 8 slices may be acquired. In other embodiments, the protocol may include different parameters.

In some embodiments, the steps 210 and 220 may be repeated for each region until all the data necessary is acquired, as shown in step 230.

After all the data is acquired, the image data for the scan(s) may be acquired in step 240.

In some embodiments, the method may optionally include a step 250 of generating image data in step 250. The image data may be generated according to known MR known techniques. In some embodiments, the generating step may further include processing the image data. In some embodiments, the image data may be corrected for attenuation and/or motion before being generated.

In some embodiments, the image data may be further processed according to known techniques so as to improve the appearance of the brain stem before the image data is generated. In some embodiments, the method 200 may include additional steps shown in FIGS. 3 and/or 4 before the image data is generated in step 250.

In some embodiments, the method 200 may include a step 260 of outputting the generated image data. In some embodiments, the outputting may include but is not limited to displaying the image(s), printing the image(s), and storing the image(s) remotely or locally. In other embodiments, the image(s) may be forwarded for further processing.

The method of acquiring image data according to embodiments overcomes the deficiencies of other neuromelanin MRI contrast techniques. The method, according to embodiments, maximizes neuromelanin contrast generated by MTC effect while manages the practical consequences of the additional delivery of electromagnetic energy resulting from the use of MTC pulses.

Processing Methods

After the image data is received, the method 100 may further include a step of 120 of processing the image data. The step 120 may optionally include one, some or all of the steps of methods 300 and/or 400 shown in FIGS. 3 and 4, respectively. In some embodiments, one, some or all of the steps of the methods 300 and 400 may be optionally included in step 250. In other embodiments, the methods 300 and/or 400 may be performed after acquiring MR image data of a subject. The steps of methods 300 and 400 may be performed automatically or may be performed with some user intervention. In further embodiments, the method 100 may include additional or alternative known post-processing methods.

The method 300 may be directed to processing the image data to register the multiple signal measurements, for example, acquired by the method 200, to remove head motion artifact. In some embodiments, the method 300 may include a step 310 of selecting one measurement without head motion artifact from the received image data. After the measurement is selected, the method 300 may further include a step 320 of aligning all of the other measurements included in the image data received to the selected measurement. In some embodiments, the aligning step 320 may be based on a linear registration technique. The linear registration technique may be any known technique, for example, 3dvolreg of the Analysis of Functional NeuroImages (AFNI). See http://afni.nimh.nih.gov/afni, which is hereby incorporated in its entirety.

After the measurements are aligned, the method 300 may include a step of 330 of discarding certain measurements. In some embodiments, the discarded measurements may include those measurements that cannot be reliably corrected, for example, those with head motion that is above a threshold, such as those with severe head motion. In some embodiments, this step may be omitted.

Next, the remaining aligned measurements may be averaged in step 340. The averaged measurements/data may then be outputted in step 350. In some embodiments, the outputting may include but is not limited to displaying the averaged measurements as image(s) and/or data, printing the averaged measurements, and storing the averaged measurements remotely or locally. In other embodiments, the averaged measurements may be outputted or transmitted for further processing and analyzing.

The method 300 allows for small amounts of motion to be corrected and significantly motion degraded measurements to be discarded. This method addresses the deficiencies associated with imaging the brain, for example, the LC and SN regions. Because LC and SN are small structures, MRI can be challenging in these locations as small amounts of motion can substantially destroy their signals.

The method 400 may be directed to processing the image data to register the each of the subject's images into a common space. In some embodiments, the method 400 may be performed using image data for which head artifacts have been removed, for example, by the method 300. In other embodiments, the method 400 may be performed using other corrected or non-corrected image data.

In some embodiments, the method 400 may include a step 410 of aligning each image (e.g., neuromelanin image) of the subject to T1 images, for example, mprage images, that cover the whole brain image. Any well-known alignment program, may be used, for example, align_epi_anat.py of AFNI may be used.

Next, the method may include step 420 of converting the image data into common space. The step 420 of converting may include converting the T1 images into a common space (e.g., Talairach space). The step 420 may also include converting the neuromelanin images of the subject into the same common space based on the aligning and converting (converting the T1 image) steps. Any well-known conversion program, may be used, for example, @auto_tlrc of AFNI may be used.

Next, the method 400 may include a step 430 of generating a mask of at least one region, for example, the SN and/or LC regions. In some embodiments, the step 430 may include binarizing the region(s) (e.g., SN and LC regions) as a mask on the neuromelanin images in the common space. Any well-known conversion program, may be used, for example, 3dcalc of AFNI may be used.

Figure 8:
FIG. 8 shows an example of a generated image.

FIG. 8 shows an example of a generated and acquired image. The image was acquired based on the following parameters: 1) a prepulse of about 9.984 ms, Flip angle of about 300°; 2) TE/TR=about 2.58/260 ms; 3) 11 contiguous slices; 4) 0.39×0.39×3 mm 5) 7 measurements; 6) Flip angle of about 40°; 7) about 470 Hz/pixel, and 8) about 12.37 scan time. This demonstrates that MTC contrast allows detection of neuromelanin containing brainstem structures.

Analyzing Methods

After the image data is received, the method 100 may optionally include a step of 130 of analyzing the image data to determine qualitative and/or quantitative information, for example, of the neurodegeneration of the subject. The information may include but are not limited to disease state, volume information of region(s) of the brain (e.g., the LC and/or SN regions of the brain), metabolic information, physiologic information, contrast to noise ratio (CNR), as well as multimodal information.

Figure 5:
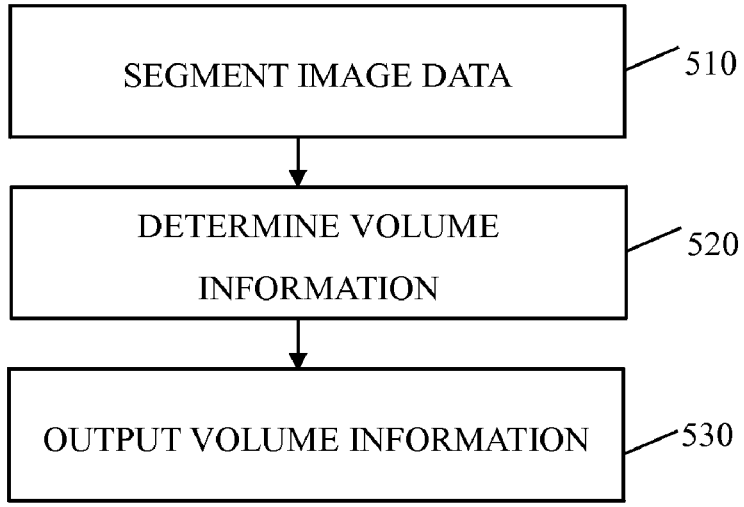
FIG. 5 shows a method of generating quantitative information.

FIG. 5 illustrates a method of determining quantitative information of at least one region of the brain, e.g., the LC and/or SN regions, according to embodiments. Quantitative information may include but is not limited to volume information, contrast-to-noise ratio (CNR) information, and/or number of voxels, as well as other types of quantitative information. For example, the CNR (e.g., MEAN) and number of voxel may substantially correspond to the amount of neuromelanin present and the number of neurons that contain neuromelanin. However, it would be understood that the step 130 of determining qualitative and/or quantitative information may include alternative or additional steps. It may include any well-known methods of determining such information.

Figure 3:
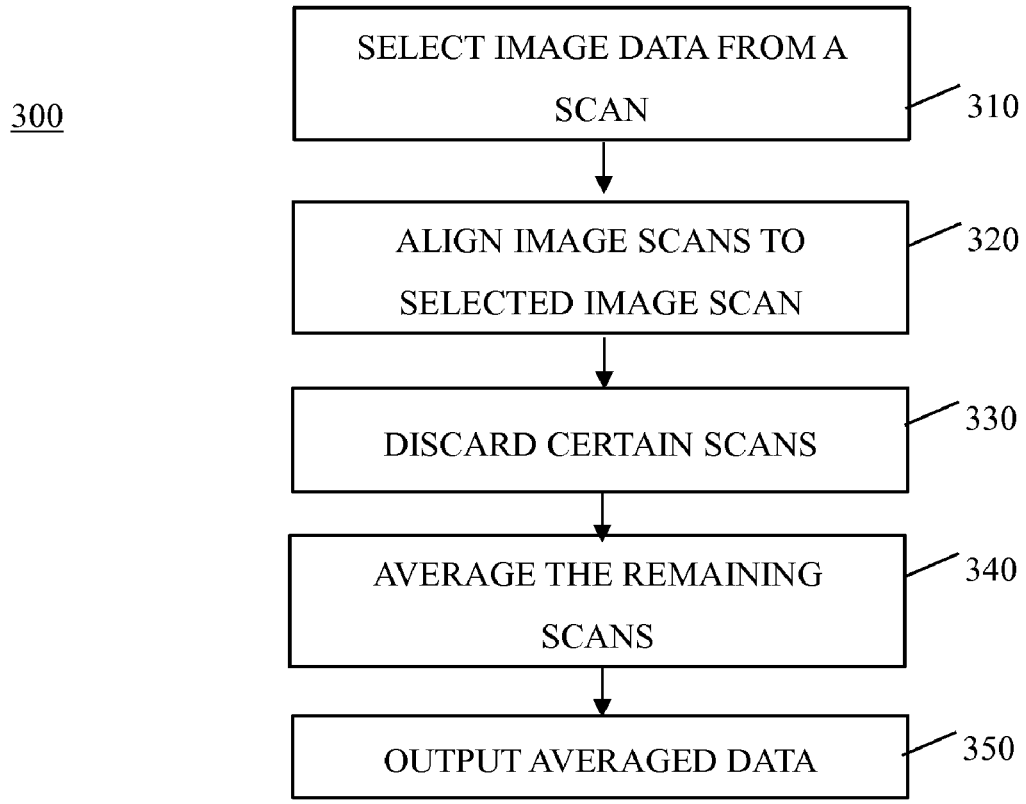
FIG. 3 shows a method of post-processing the acquired image data.

In some embodiments, the method 500 may further include a step 510 of further processing the image data. In some embodiments, the processing step 510 may include automatically segmenting the image data for a specific region, for example, the LC and/or SN of the brain. In some embodiments, the image data may be initially registered to remove head motion artifact, for example, as shown in FIG. 3. In some embodiments, the step 510 may be included in the method 300.

In some embodiments, the processing step 510 may be a global region-based segmentation. In some embodiments, the step 510 may include causing the boundary of that region to be discontinuous. In some embodiments, the segmenting step may include applying a region-based snake algorithm, such as the Chan-Vese algorithm. See, for example, Tony F. Chan et al., "Active Contours without Edges," IEEE Trans Image Proc 2001; 10(2):266-277, which is hereby incorporated in its entirety.

The step 510 may include defining a number (e.g., two) regions of interest (ROI)s, corresponding to the LC and/or SN on each side based on known landmarks. These landmarks may be identified, for example, by known neuroanatomic and stereologic study of those regions. See D. C. German, et al, "The Human Locus Coeruleus: Computer Reconstruction of Cellular Distribution," J. Neurosci., 8 (1988), 1776-88, which is hereby incorporated in its entirety. Then, the segmenting step 510 may include applying an active contour technique to the ROIs, which are known to contain the region, e.g., the LC and/or SN. This may result in the ROIs being 10× interpolated in each dimension to increase the smoothness of the contour because not many pixels would be contained in the region at a given MR imaging resolution.

In some embodiments, the step 510 may be optimized. For example, the input parameters to the algorithm may be optimized in such a way that the segmented region (e.g., LC and/or SN regions) resembles an actual region (e.g., LC and/or SN) by radiologists' readings. Then, these parameters may be used throughout the image processing as all (e.g., LC and/or SN) images from 2D gradient-echo (GRE) imaging with MTC would provide similar image intensities and overall contrast.

Figure 9:
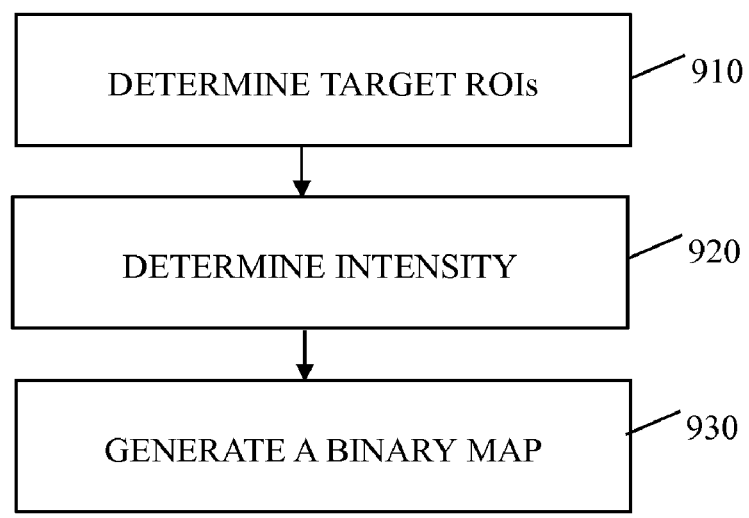
FIG. 9 shows an method of processing the image data.

In some embodiments, the step 510 may include other methods of segmentation. FIG. 9 illustrates a method 900 of segmentation according to some embodiments. In some embodiments, the image data may be initially registered to remove head motion artifact, for example, as shown in FIG. 3. In some embodiments, the step 510 may be included in the method 300.

As shown in FIG. 9, the method 900 may include a step 910 of disposing a number of target regions of interests (ROI) corresponding to the region. In some embodiments, the target ROIs may be a circle having a diameter of about 6 mm. In other embodiments, the target ROIs may have a different shape. In some embodiments, the number of target ROIs may be about 2 ROIs for each slice. In other embodiments, there may be more or less target ROIs for each slice. In some embodiments, target ROIs may be disposed for 4 consecutive slices starting from the bottom or top slice. In other embodiments, target ROIs may be disposed for more or less slices.

In each slice, the target ROIs may be disposed in areas surrounding the region. For example, for LC, target ROIs may be placed in the pons close to the possible LC locations. The LC locations may be disposed from top one in which the fourth ventricle just appears. There may be 2 ROIs for each slice, one disposed in the left and one disposed in the right pons.

For example, for SN, the target ROIs may be placed in tissues surrounding the SN. For example, for LC, target ROIs may be placed in the pons close to the possible LC locations. The LC locations may be disposed from top one in which the fourth ventricle just appears. There may be 2 ROIs for each slice, one disposed in the left and one disposed in the right pons.

For example, for the SN, target ROIs (with circles of about 6 mm) can be disposed in tissues surrounding the SN for 4 consecutive slices, starting from the bottom one, which barely showed the SN. For each slice, 2 ROIs can be disposed flanking both the right and left SNs.

After, the target ROIs are disposed, the method 900 may include a step 920 determining signal intensity for each Target ROIs. In some embodiments, the step 920 may include first verifying that the voxel intensities for the ROIs as approximately normally distributed.

In some embodiments, the step 920 may include determining the Mean ($I_{mean}$) and, standard deviation ($I_{sd}$) of signal intensity for the target ROIs. The intensity difference ($I_{diff}$) for each voxel may then be calculated. The intensity difference ($I_{diff}$) for each voxel may be calculated using the following: $I_{diff}=I_{voxel}-I_{mean}-X \times I_{sd}$ for each voxel. X may depend on the region to be analyzed. For example, for SN, X may be 3; and for LC, x may be 4.

Next, the method 900 may include a step 930 of generating a binary map. A binary map may be generated based on the following: a binary map was generated in this way: if $I_{diff}>0$, then $B_{voxel}=1$; otherwise, $B_{voxel}=0$. The voxels with $B_{voxel}=1$ may be considered to substantially corresponds to neuronal tissue containing neuromelanin. Next, the step 930 may include defining the ROIs on the binary map. In some embodiments, the ROIs may be confined. For example, for the LC, the ROIs may be confined in two circles (6 mm in diameter, centered 3 mm lateral and 2 mm posterior to the apex of the fourth ventricle, one on the left and one on the right).

Figure 4:
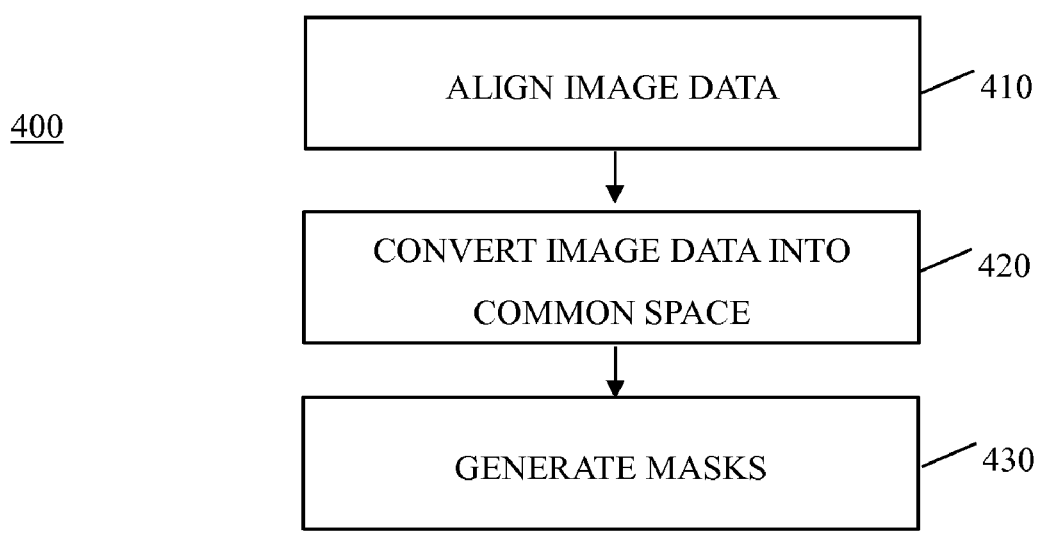
FIG. 4 shows another method of post-processing the acquired image data.
Figure 10:
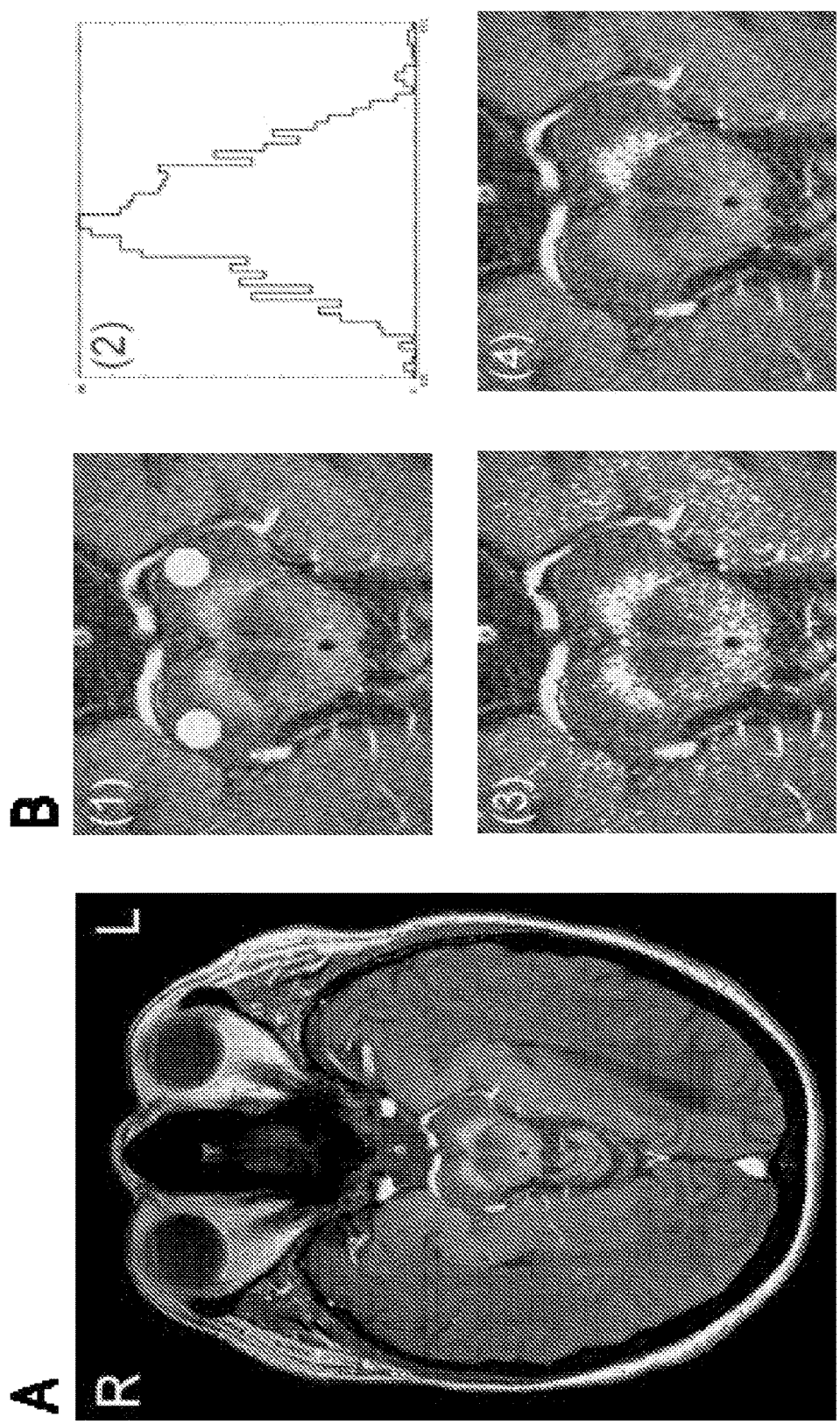
FIGS. 10(A) and (B) show an example of a generated image.

FIGS. 10A and 10B show an example of an image of the SN. FIG. 10A shows an image from a subject showing the SN. The image was acquired using a 3.0 Tesla Siemens Magnetom TRIO scanner (Siemens Medical Solutions, Malvern, Pa.) using a 2D gradient echo sequence with magnetization transfer contrast (MTC) preparation pulse. The sequence parameters were as follows: TR=335 ms, TE=2.68 ms, 15 slices, slice thickness=3.0 mm, FOV=200 mm, matrix size=512×416, 1 average, 7 measurements, flip angle=40°, and bandwidth=470 Hz/Px. Imaging data were analyzed with AFNI[2]. All images from the 7 measurements were registered to the first one, and then averaged. FIG. 1B-1 shows target ROIs (circles with diameter in 6 mm) placed in the tissues surrounding the SN for 4 consecutive slices, starting from the bottom one which barely showed the SN. Each slice has 2 ROIs, flanking both the left and right SNs. FIG. 10B-2 shows voxel intensities of these ROIs that were verified as approximately normally distributed. FIG. 10B-3 shows a generated binary map. FIG. 10B-4 shows ROIs for the SN that were defined on the binary map, which did not require an accurate delineation of the SN.

In some embodiments, after the region has been segmented, the method may optionally or additionally include a step 520 of determining quantitative information. In some embodiments, the determining may include determining volume information. The volume information may include any one, some or all, but is not limited to the volume of at least one region of the brain (e.g., LC and/or SN), or the voxels identified as the region (e.g., LC and/or SN). In some embodiments, the volume information may be an estimate of the volume. In some embodiments, the volume may be the product of the number of segmented voxels and the volume of a single voxel (V=number of voxels×voxel size). In other embodiments, the determination of the volume information may be based on other known volume algorithms In other embodiments, the step 520 may include determining contrast-to-noise ratio (CNR) information incorporating both detected area and intensity values within the area ($CNR_{voxel}=(I_{voxel}-I_{mean})/I_{sd}$). In some embodiments, the MEAN CNR may be determined for the region. In some embodiments, the step 520 may include determining number of voxels may be calculated for the region. The MEAN CNR and number of voxel may substantially correspond to the amount of neuromelanin present and the number of neurons that contain neuromelanin. In other embodiments, the determination of the contrast-to-ratio information may be based on other contrast-to-noise ratio algorithms. In some embodiments, the step 520 may include determining other quantitative information.

In some embodiments, the method may further include a step 530 of outputting the quantitative information. In some embodiments, the quantitative information may be outputted with the image data in step 160. In some embodiments, the outputting may include but is not limited to displaying the quantitative information, printing the quantitative information, and storing the quantitative information remotely or locally. In other embodiments, the quantitative information may be forwarded for further processing. The quantitative may also include the voxels identified as the region of interest, e.g., LC and/or SN.

In some embodiments, the method 100 may optionally include a step 140 of classifying the quantitative and/or qualitative information. In some embodiments, the information may be compared to previous information of the subject, for example, to provide information regarding the progression of the disease. In some embodiments, the information may be compared to information associated with many subjects, e.g., an atlas. The comparing may include comparing the information to a predetermined ranges associated with the information, each range being associated with a different disease state and/or progression of the disease state. The disease state may include but is not limited to Parkinson's disease, progressive supranuclear palsy, Pick's disease, Alzheimer's disease, and Down's syndrome, as well as psychiatric disorders. The disease state may be based on any known scale.

In some embodiments, the method may further include a step 150 of outputting the results. In some embodiments, the results may include the information, the processed image data, and/or the image(s) based on the processed image data. The information may include any one, some or all, but is not limited to the quantitative information of the region (e.g., LC and/or SN) (e.g., volume, CNR, number of voxels, etc.), the classification of the information with respect to previous information of the subject and/or prestored information associated with different disease states and/or progression of the disease state, and the like. In some embodiments, the outputting may include but is not limited to displaying the results, printing the results, and storing the results remotely or locally. In other embodiments, the results may be transmitted for further processing.

Atlas Generation Method

Figure 6:
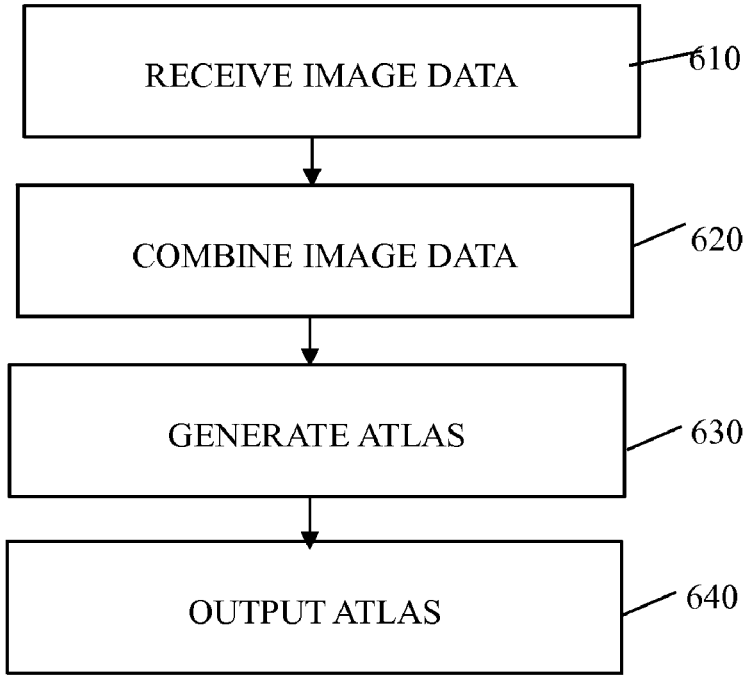
FIG. 6 shows a method of generating an atlas.

In some embodiments, the processed image data may be used to generate an atlas for the a region, for example, SN and/or LC. FIG. 6 shows a method 600 according to embodiments to generate an atlas of region(s) of the brain stem, for example, the SN and/or the LC.

In some embodiments, the method may include a step 610 of receiving image data for a plurality of subjects. In some embodiments, the image data may have been already processed to generate masks for the SN and/or LC. In other embodiments, the step 610 may include the steps provided in the method 400.

The method 600 may include a step 620 of combining the image data for a plurality of subjects in the common space. In some embodiments, the combing technique may be any known technique, for example, 3dcalc of the Analysis of Functional NeuroImages (AFNI).

The method 600 may include a step 630 of generating the atlas. The step 630 may include overlaying the combined masks onto T1 images in the common space.

The method may include a step 640 of outputting the atlas. In some embodiments, the outputting may include but is not limited to displaying the results (e.g., combined masks onto 2D T1 images), printing the results, and storing the results remotely or locally. In other embodiments, the results may be transmitted for further processing.

System Implementation

Figure 7:
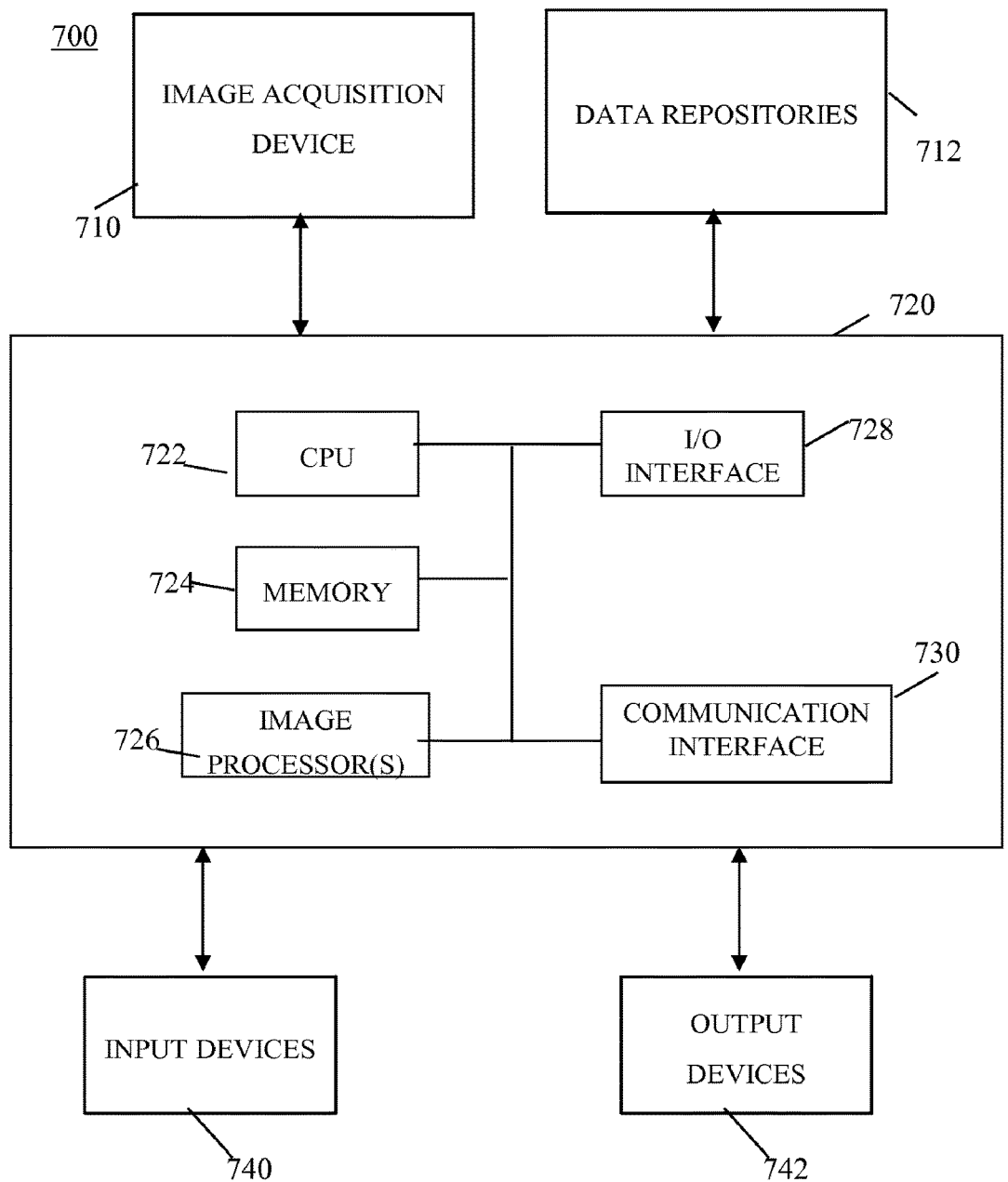
FIG. 7 shows a system configured to process an image of a brain to optionally generate information.

FIG. 7 shows an example of a system 700 for processing and generating image data and determining information. The system for carrying out the embodiments of the methods disclosed herein is not limited to the system shown in FIG. 7. Other systems may be used.

The system 700 may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

Although the modules of the system are shown as being directly connected, the modules may be indirectly connected to one or more of the other modules of the system. In some embodiments, a module may be only directly connected to one or more of the other modules of the system.

It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the system may be time synchronized. In further embodiments, the system may be time synchronized with other systems, such as those systems that may be on the medical facility network.

In some embodiments, the system 700 may include an image acquisition device 710 configured to acquire the image data of a subject. The image acquisition device 710 may be any device configured to generate and acquire images from a magnetic resonance imaging (MRI) scan. The image acquisition device 710 may be any known MR dedicated system capable of Gradient Echo imaging. In some embodiments, the MR system may be a 3T MR system. In other embodiments, the system 700 may communicate with the imaging systems and/or a data storage device. For example, the system may include one or more data repositories 712, such as radiological image storage (e.g., Picture Archiving and Communication System (PACS)).

In some embodiments, the image acquisition device 710 may include a computer system to carry out the image processing. The computer system may further be used to control the operation of the system or a separate system may be included.

The system 700 may include a computer system 720 to carry out the image processing, generating and/or analyzing. In some embodiments, the computing system 720 may be a separate device. In other embodiments, the computing system 720 may be a part (e.g., stored on the memory) of other modules, for example, the image acquisition device 710, and controlled by its respective CPUs. The computer system 720 may further be used to control the operation of the image acquisition device 710 or a computer separate system may be included.

The computer system 720 may also be connected to another computer system as well as a wired or wireless network. The computer system 720 may receive or obtain the image data from the image acquisition device 710 or from another module, such as a hospital server provided on a network.

The system 720 may be a computing system, such as a workstation, computer, or the like. The system 720 may include one or more processors 722. The processor(s) 722 (also referred to as central processing units, or CPUs) may be any known central processing unit, a processor, or a microprocessor. The CPU 722 may be coupled directly or indirectly to one or more computer-readable storage medium (e.g., memory) 724. The memory 724 may include random access memory (RAM), read only memory (ROM), disk drive, tape drive, etc., or a combinations thereof. The memory may also include a frame buffer for storing image data arrays. The CPU 722 may be configured to control the image acquisition and may be configured to process the acquired images. In some embodiments, the CPU 722 may be capable of performing the image processing functionality. In other embodiments, the system may include a separate CPU for performing the image processing functionality.

In some embodiments, the CPU 722 may be configured to process the image data acquired from the image acquisition device 710. In some embodiments, the system 700 may include one or more image processors 726 (e.g., any known processing unit such as a CPU, a processor, or a microprocessor) configured to process raw image data. The processed data and results may then be stored in the memory 724. In some embodiments, another computer system may assume the image analysis or other functions of the CPU 722 or image processor 726. In response to commands received from the input device, the image data stored in the memory 724 may be archived in long term storage or may be further processed by the image processor and presented on a display.

In some embodiments, the disclosed methods (e.g., FIGS. 1-6 and 9) may be implemented using software applications that are stored in a memory and executed by a processor (e.g., CPU) provided on the system. In some embodiments, the disclosed methods may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system. In addition, various other peripheral devices may be connected to the computer platform such as an additional data storage device, a printing device, and other I/O (input/output) devices.

In some embodiments, the system 720 may include a communication interface 730 configured to conduct receiving and transmitting of data between other modules on the system and/or network. The communication interface 730 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 700 may include an input/output interface 728 configured for receiving information from one or more input devices 740 (e.g., a keyboard, a mouse, and the like) and/or conveying information to one or more output devices 742 (e.g., a printer, a CD writer, a DVD writer, portable flash memory, etc.). In some embodiments, the one or more input devices 740 may configured to control the generation of the images, display of images on a display, and/or printing of the images by a printer interface.

It is to be understood that the embodiments of the disclosure be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for generating information associated with an image of at least one region of a subject, comprising:
receiving image data of a subject acquired by at least one magnetic resonance (MR) scan that included a pre-pulse signal and a pulse sequence, the pre-pulse signal having a flip angle between 150° and 425°;
segmenting the image data to determine at least one region;
determining at least quantitative information associated with the at least one region;
wherein the quantitative information includes a number of voxels and contrast-to-noise ratio (CNR) information;
wherein the CNR and the number of voxels correspond to an amount of neuromelanin in the region and a number of neurons that contain neuromelanin, respectively; and
outputting information associated with the at least one region, the information being based on at least the quantitative information;
wherein the image data is magnetization transfer contrast (MTC) image data acquired by a 3T MR imaging system.

2. The method according to claim 1, wherein the at least one region includes at least one of the substantia nigra pars compacta, locus ceruleus, ventral tegmental area, or raphe nuclei.

3. The method according to claim 1, further comprising:
registering the image data to a common space before the determining the quantitative information, the registering including:
registering the image data to remove head motion artifact; and aligning the image data to T1 image data.

4. The method according to claim 1, wherein the image data received in the receiving includes a plurality of signal measurements and the method further comprises:
processing the image data received in the receiving to remove head motion artifact before the determining the quantitative information, the processing including:
selecting a signal measurement without the head motion artifact from the plurality of signal measurements;
aligning all of other signal measurements to the selected signal measurement;
comparing each aligned signal measurement to a threshold; and
averaging one or more aligned signal measurements that are below the threshold.

5. The method according to claim 1,
wherein the information includes disease state, volume information, metabolic information, and/or physiologic information.

6. The method according to claim 1, further comprising:
determining a disease state of the subject using the quantitative information, the determining the disease state including comparing the quantitative information to at least one of previous information of the subject or prestored information;
wherein the information includes the disease state.

7. The method according to claim 1, wherein the quantitative information further includes volume information.

8. A method for generating information associated with an image of at least one region of a subject, comprising:
receiving image data of one or more target regions of a subject including magnetization transfer contrast (MTC) image data of a subject acquired by at least one magnetic resonance (MR) scan that included a pre-pulse signal and a pulse sequence, the pre-pulse signal having a flip angle between 150° and 425°;
determining a signal intensity value for each voxel in each target region from the MTC image data;
segmenting the MTC image data to determine at least one region based on the signal intensity value for each voxel in corresponding target region; and
determining at least quantitative information, related to neuromelanin contained in the at least one region, associated with the at least one region using the MTC image data, the quantitative information including a number of voxels and volume information determined from the number of voxels; and
outputting information associated with the at least one region, the information being based on at least the quantitative information.

9. The method according to claim 8, wherein the at least one region includes at least one of the substantia nigra pars compacta, locus ceruleus, ventral tegmental area, or raphe nuclei.

10. The method according to claim 8, wherein the segmenting includes:
generating a binary map using the signal intensity value for each voxel;
wherein each voxel of the binary map with $B_{voxel}=1$ corresponds to neuron containing neuromelanin.

11. The method according to claim 8, wherein the quantitative information includes contrast to noise information (CNR) information and the CNR information corresponds to an amount of neuromelanin in the at least one region, respectively.

12. The method according to claim 8, wherein the number of voxels corresponds to a number of neurons that contain neuromelanin.

13. The method according to claim 8, further comprising:
determining a disease state of the subject using the quantitative information, the determining the disease state including comparing the quantitative information to at least one of previous information of the subject or prestored information.

14. The method according to claim 13,
wherein the information includes the disease state.

15. The method according to claim 8, wherein the flip angle is between 250° and 350°.

* * * * *